United States Patent
Conrads et al.

(10) Patent No.: US 6,796,196 B2
(45) Date of Patent: Sep. 28, 2004

(54) ARRANGEMENT FOR DEFINING THE CARBON CONTENT OF ASH

(75) Inventors: Hans Georg Conrads, Hanover (DE); Volkhard Klupsch, Barleben (DE)

(73) Assignee: PROMECON Prozess- & Messtechnik Conrads GmbH., Barleben (DE)

( * ) Notice: Subject to any disclaimer, the term of this patent is extended or adjusted under 35 U.S.C. 154(b) by 134 days.

(21) Appl. No.: 10/234,226

(22) Filed: Sep. 4, 2002

(65) Prior Publication Data

US 2004/0041553 A1 Mar. 4, 2004

(51) Int. Cl.$^7$ .......................... G01M 19/00; G01N 29/00
(52) U.S. Cl. ........................ 73/865.8; 73/64.53
(58) Field of Search .................. 73/865.8, 866, 73/64.53, 61.75; 702/23, 24, 25; 324/633, 636

(56) References Cited

U.S. PATENT DOCUMENTS

| | | | |
|---|---|---|---|
| 4,498,338 A | * | 2/1985 | Peltonen et al. ........... 73/865.8 |
| 4,775,516 A | * | 10/1988 | Kempster et al. ............. 422/80 |
| 5,729,470 A | * | 3/1998 | Baier et al. .................... 702/24 |

FOREIGN PATENT DOCUMENTS

| | | |
|---|---|---|
| DE | 33 03 177 | 8/1983 |
| DE | 198 56 870 | 6/1999 |
| SU | 1122960 | * 11/1984 |
| SU | 1158911 | * 5/1985 |
| SU | 1231323 | * 5/1986 |

* cited by examiner

*Primary Examiner*—Helen Kwok
(74) *Attorney, Agent, or Firm*—Karl Hormann

(57) ABSTRACT

An arrangement for measuring the carbon content of fly ash consisting of a modified coaxial resonator including an elongated arch-shaped member and an elongated conductor mounted coaxially therein and a generator for generating vibrations of variable frequency therebetween and a device for measuring attenuations in the vibrations for deriving a measure of the carbon content of ash moving between the arch-shaped member and the elongated member.

6 Claims, 1 Drawing Sheet

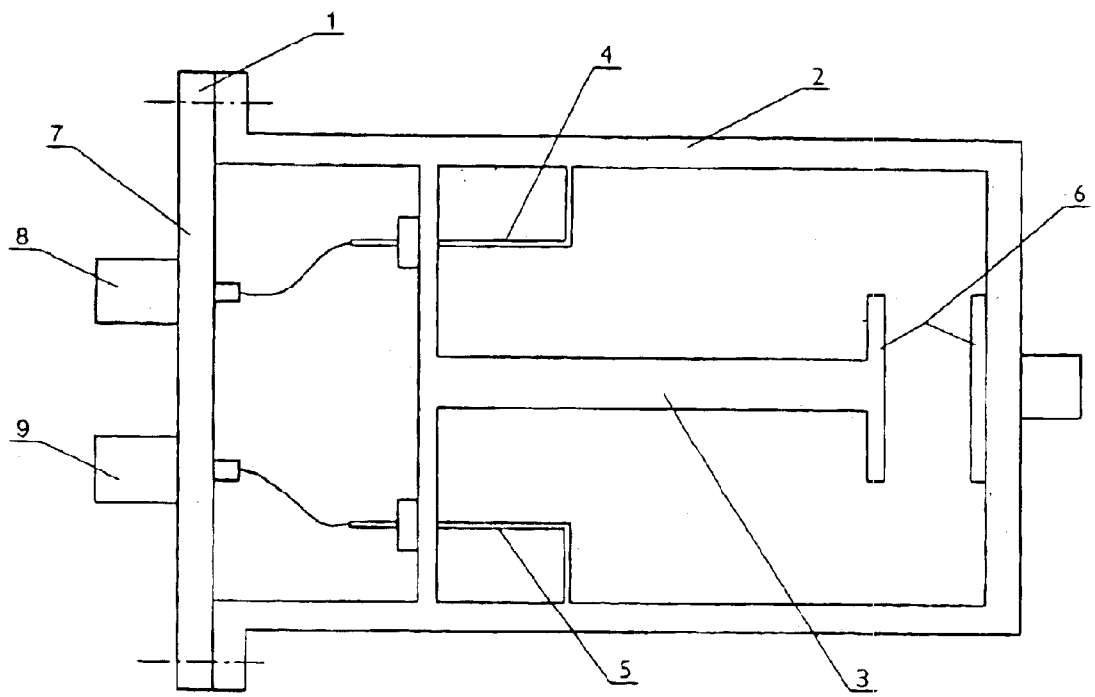
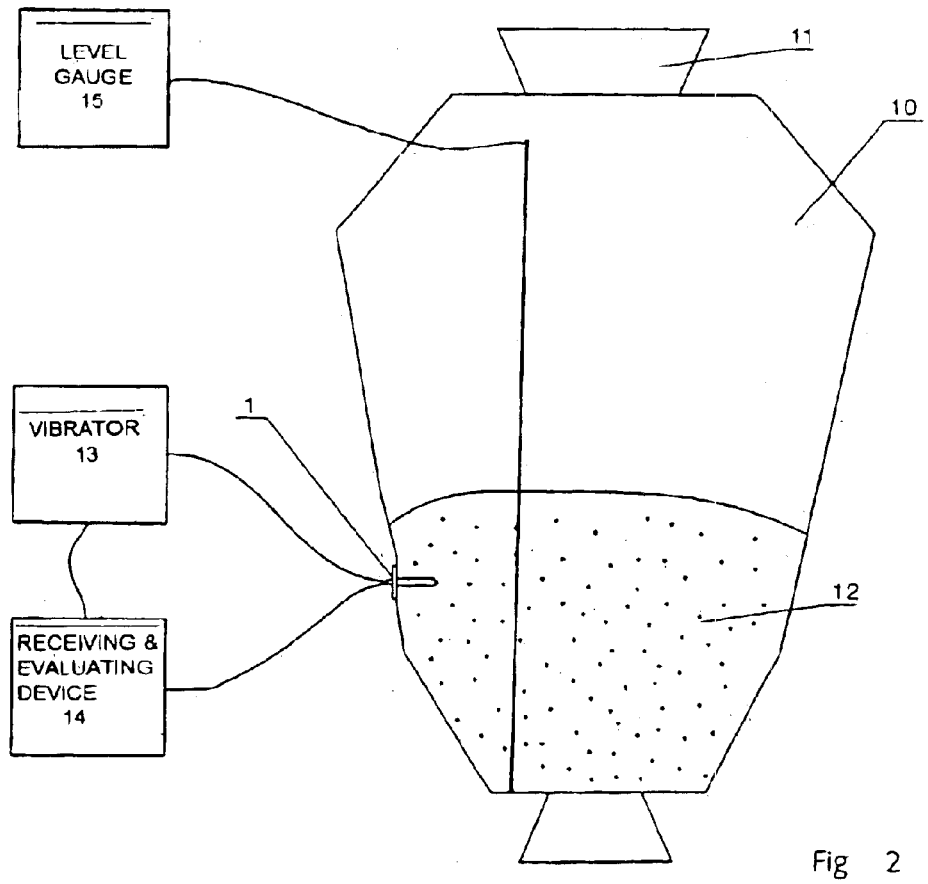

ARRANGEMENT FOR DEFINING THE CARBON CONTENT OF ASH

BACKGROUND OF THE INVENTION

1. Field of the Invention

The invention, in general, relates to an arrangement for defining the carbon content of ash and, more particularly, it relates to an arrangement for defining the carbon content of filter or fly ash provided as a compact fill in collection containers, for instance. While not limited to this field, a preferred field of application of the invention pertains to furnaces of coal-fired power plants. The invention may, however, be advantageously practiced wherever it is necessary or desirable to define the carbon content of compacted ash. In addition to coal-fired power plants, the invention may be practiced in connection with refuse incinerators or operations in which ash is used as an additive.

2. The Prior Art

Defining the carbon content of ash and, more particularly, of filter or fly ash, is necessary for controlling or optimizing combustion processes in order to utilize to the fullest possible extent the energy contained in fuel. It is also important to control the quality of ash used as an additive, for instance, in the construction and cement making industries. In either case, it is desirable to achieve as low a carbon or residual fuel content as possible. Changing load conditions in combustion equipment and different fuel compositions require continuous monitoring of the combustion process. This necessitates defining the residual carbon content of combustion waste either as continuously as possible or periodically at short intervals.

At present, the methods used in combustion equipment of coal-fired power plants usually involve taking samples of ash for subsequent analytical examination in a remote laboratory. Not only are such methods expensive, they also lead to significant delays which for all intents and purposes renders impossible any optimized control of the combustion process.

For that reason, efforts have not been lacking for some time to develop methods and apparatus for defining, in a simple manner, continuously or periodically without delay, the residual carbon content of fly ash. In this connection, methods of evaluating, by distributed electrical parameters, changes in the electrical values of devices for receiving the ash, have been found to be particularly useful. Problems have, however, arisen in connection with the handling or feeding of ash into such devices. The reason for those problems reside in the extremely complex compaction behavior of fly ash.

For instance, German laid-open patent specification 33 03 177 discloses a method and an apparatus for measuring the carbon content of fly ash by evaluating changes in the capacitance of a capacitor into which fly ash is introduced as a dielectric substance. Fly ash is taken from a silo and transferred to a measuring chamber forming the dielectric medium of a capacitor wherein it is compacted by vibration. After the capacitance of the capacitor has been defined, the fly ash is removed from the measuring chamber and returned to the silo. The carbon content of the fly ash is deduced as a function of the electrically measured capacitance of the capacitor. The method may be practiced continuously or periodically; but for attaining useful measurement results a substantially constant average quantity of fly ash in the measuring chamber is required.

Another way of evaluating changes in electrical values has been described in German laid-open patent specification 198 56 870. Ash transported by a pneumatic feed system is conveyed to a microwave resonator. The particle content of the sample is detected by means of an exhaust filter and a light barrier and is brought to predetermined values by a vibrator. In addition, the sample is set to a predetermined temperature. The carbon content is defined in a known manner by a microwave resonance technique. After evaluation, the sample is returned to the pneumatic feed system.

The described methods in accordance with the prior art require complex apparatus for taking, preparing and returning samples. The complexity is owing not least to the extremely poor compacting behavior of the filter or fly ash.

OBJECT OF THE INVENTION

It is an object of the invention to provide a simple arrangement for measuring the carbon content of filter or fly ash by evaluating any change in the electrical parameters of an electrically vibrating device for receiving the ash.

A more particular object of the invention is to provide an arrangement of the kind referred to which avoids any complexity in the taking, preparation and return of samples.

Other objects will in part be obvious and will in part appear hereinafter.

SUMMARY OF THE INVENTION

In accordance with a currently preferred embodiment of the invention there is provided an arrangement for defining the carbon content of ash by evaluating changes in the electrical parameters of an electrically vibrating device wherein the ash is received and which is provided with distributed electrical impedances, means for generating variable frequency electrical vibrations and means for evaluating electrical resonance, wherein the electrically vibrating device for receiving the ash consists of a coaxial resonator modified in its exterior confining wall by at least one intake and output opening for ash, the coaxial resonator being placed in compacted ash such that a representative sample of the ash passes through the interior of the modified coaxial resonator and wherein the modified coaxial resonator is electrically connected to means for generating the variable frequency electrical vibrations and to means for evaluating any electrical resonance.

More particularly, a coaxial resonator modified in its confining wall by at least two openings is placed within compacted ash such that a representative portion of the ash the carbon content of which is to be defined passes through the interior of the coaxial resonator. As well as with means for generating electrical vibrations of variable frequency the modified coaxial resonator is electrically connected to means for evaluating electrical resonances. Preferably, the confining wall of the modified coaxial resonator is configured as a closed metallic arch or bow within which is there is disposed a rod-shaped interior conductor or electrode. The free or exposed forward end of the conductor forms a capacitor either with the confining wall or with an element mounted thereon. The dielectric medium of the capacitor is formed or constituted by the fly ash present in the modified coaxial resonator. As a result of its structure, the modified coaxial resonator is characterized by very large openings for the intake and output of ash, relative to its geometric dimensions. Thus, by placing the modified coaxial resonator in compacted ash in an ash collection container, the ash can satisfactorily move through the resonator without forming bridges or barriers when the container is partially or completely emptied.

It has been found that by placing the modified coaxial resonator in compacted ash, the density of the ash is substantially constant regardless of the height of the dumping level of the ash so that the measurement results are sufficiently exact and reproducible.

For defining the carbon content of the fly ash, changes are examined in the electrical resonance of the modified coaxial resonator filled with ash, relative to calibratory measurements or reference signals. In this connection, it has surprisingly been found that it is of particular importance that the quality of the coaxial resonator modified by large openings in its confining wall be such that even changes in the carbon content of less than 0.1% may be accurately defined at undue complexity.

It is particularly useful so to place the modified coaxial resonator in a lower section of an ash collection container that as the container is filled with ash, a representative portion of the ash automatically slides into the interior of the coaxial resonator and, more particularly, into that section at the interior conductor which is structured as a capacitor. As soon as the modified coaxial resonator is completely covered with ash and the ash in the section of the coaxial resonator has quieted, the density of the ash in the coaxial resonator is in a sufficiently constant state and defining the carbon content may take place, drawing on the dielectric properties of the carbon, by defining the resonant frequency of the modified coaxial resonator. For determining whether the coaxial resonator is completely covered by ash, it may be useful to place a filling level gauge into the ash collecting container.

In conventional combustion furnaces of power plants the temperature of filter or fly ash in ash collection containers is in the range of from about 60 to about 90° C. (140 to 194° F.). Hence, it is above the dew point and humidity induced distortions of measurement results are practically impossible.

For defining the carbon content it is advantageous to take comparative measurements of input and output of ash into or from the ash collection container at short intervals and to compare the results of several successive measurements. Large deviations between results of immediately successive measurement indicate that the ash in the coaxial resonator is still in motion and that its density is not constant. By contrast, almost uniform successive measurement results indicate that the ash in the coaxial resonator has quieted. A definition of the carbon content can reasonably be obtained only on the basis of the latter measurements. In a practical operation, i.e., at real intervals of input and output of ash into or from the ash collection container, sufficiently accurate measurement results were obtained at 2 to 5 measurements per minute.

The special advantage of the arrangement in accordance with the invention resides in its simple and sturdy construction and, more particularly, in the possibility of installing it directly into a fly ash receiving container. The need in prior art arrangements for complex handling of ash (removal of ash samples from a container or conveyor system, providing measurement samples of predetermined size and density; providing predetermined temperature conditions; return of the sample) has thus been effectively overcome.

DESCRIPTION OF THE SEVERAL DRAWINGS

The novel features which are considered to be characteristic of the invention are set forth with particularity in the appended claims. The invention itself, however, in respect of its structure, construction and lay-out as well as manufacturing techniques, together with other objects and advantages thereof, will be best understood from the following description of preferred embodiments when read in connection with the appended drawings, in which:

FIG. 1 is a top elevational view of a modified coaxial resonator in accordance with the invention; and FIG. 2 is the arrangement of a modified coaxial resonator within an ash collecting container.

DESCRIPTION OF THE PREFERRED EMBODIMENT

The confining wall of the modified coaxial resonator shown in FIG. 1 is defined by an elongated bow or arch 2 made of steel. An interior conductor or electrode 3 and two induction coils 4 and 5 are positioned within the arch 2. The free end of the interior conductor or electrode 3 is of disc-like configuration and forms a capacitor 6 with a plate mounted on the arch 2. The arch 2 is provided with a mounting flange 7 supporting two connectors 8 and 9 for the input and output of electrical signals. The inputs of the induction coils 4 and 5 are electrically insulated from the arch 2; but they are electrically connected with the connectors 8 and 9. The space between the confining wall 2 and the conductor 3 forms a input and output opening or aperture through which ash may slide whenever it is moving within the container 10.

As shown in FIG. 2, the modified coaxial resonator is arranged at a lower section of an ash collection container 10 such that a representative portion of ash 12 entering into the container 10 can move into the interior of the modified coaxial resonator 1 and, hence, between the plates of the capacitor 6. The induction coil 4 is electrically connected to a vibrator 13, and the induction coil 5 is electrically connected to a receiving and evaluation device 14. A gauge 15 for measuring the height or level of ash within the container may be provided as advantageous auxiliary equipment.

The oscillator 13 generates a variable frequency electrical vibration at 5 second intervals. The vibration lies within the resonant range of the modified coaxial resonator 1 and is coupled into it by way of the induction coil 4. The induction coil 5 receives the electrical vibrations of the modified coaxial resonator 1 and feeds them to the receiving and evaluating device 14. The receiving and evaluating device 14 defines the attenuation curve of the modified coaxial resonator and of the resonant frequency with reference to the variable frequency vibrations generated by the vibrator 13. Where the resonant frequency remains substantially constant over several consecutive, it may be assumed that the ash 12 within the ash collection container 10 has quieted and is sufficiently condensed (similar to a dumped pile). The carbon content of the ash 12 may than be defined on the basis of the resonant frequency with reference to calibratory measurements or reference signals. Because of the large opening of the modified coaxial resonator 1 at a relatively small height of the arch 2 any ash 12 present in the modified coaxial resonator 1 will automatically slide out of the resonator 1 whenever ash is removed from the ash collection container 10 while new ash slides into the resonator 1. In this manner, a representative portion or sample of ash from the container 10 will constantly be fed into the interior of the modified coaxial resonator 1.

What is claimed is:

1. An arrangement for defining the carbon content of ash, comprising:

an elongated arch-shaped member adapted to be mounted in a pile of ash and forming input and output openings for moving ash therethrough;

an elongated rod-shaped conductor mounted substantially coaxially within the arch-shaped member;

means for generating variable frequency vibrations between the arch-shaped member and at least an end portion of the elongated conductor; and means for receiving and evaluating changes in the vibrations relative to reference signals for deriving therefrom a measure of the carbon content of the ash.

2. The arrangement of claim 1, wherein the means for generating variable frequency vibrations comprises a first induction coil and a vibrator.

3. The arrangement of claim 1, wherein the means for receiving and evaluating changes comprises a second induction coil and an evaluation device.

4. The arrangement of claim 1, wherein the end portion of the elongated rod-shaped conductor comprises a first plate and wherein the arch-shaped member comprises a second plate mounted opposite the first plate.

5. The arrangement of claim 1, wherein the pile of ash is contained in an ash collection container.

6. The arrangement of claim 5, wherein the container is provided with means for measuring the height of the pile.

* * * * *